_United States Patent_ [19]

Artiss et al.

[11] Patent Number: 4,784,945

[45] Date of Patent: Nov. 15, 1988

[54] METHOD FOR DETERMINING LIPIDS

[75] Inventors: Joseph D. Artiss, Windsor, Canada; Dennis Bozimowski, Ballwin, Mo.; Robert J. McEnroe, Royal Oak; Bennie Zak, Southfield, both of Mich.

[73] Assignee: Board of Governors of Wayne State University, Detroit, Mich.

[21] Appl. No.: 925,720

[22] Filed: Oct. 30, 1986

[51] Int. Cl.$^4$ .......................... C12Q 1/26; C12Q 1/34; C12Q 1/28; G01N 33/92

[52] U.S. Cl. .......................................... 435/25; 435/11; 435/18; 435/19; 435/28; 435/803; 436/71; 436/907

[58] Field of Search .................. 435/11, 18, 25, 28, 435/803, 19; 436/71, 907

[56] References Cited

U.S. PATENT DOCUMENTS 4,680,259  7/1987  Cumbo et al. .................. 435/11

OTHER PUBLICATIONS

Elias, J. M., Am. J. Clin. Path., V. 73, (1980), pp. 797–799.
Willoughby, E. W. et al., Anal. Biochem., V. 130, (1983), pp. 353–358.
Gluck, et al., Clin Perinatol 1, 125–131 (1974).
McGowan, et al., J. Clin. Chem. Clin Biochem, 20, 807–812 (1982).
McGowan et al., Clin. Chem. 29, 1513–1517 (1983).
Gluck, L., et al., Am J. Obstet Gynecol Ref 120, 142–155 (1974).
Kolins, et al., Clin. Chem. 26, 403–405 (1980).
Nakamura, et al., Anal. Biochem. 142, 406–410 (1984).
Tietz (ed), _Fundamentals of Clinical Chemistry_, (1976) pp. 161–162.
Ambrosetti, P., Chromatographic 9(12), 633–634 (1976).
Artiss, J. D., Annals of Clin. and Lab Science 15, 488–494 (1985).
Hans, et al., Korean J. Biochem 17(1), 19–30 (1985).
Higashi, H, Siekagaku 57(2), 133–135 (1985).
Artiss, et al., Clinical Chem 30, 534–537 (1984).
McGowen et al., Microchemical Journal 31, 216–223 (1985).
Bozinowski et al., Microchemical Journal 32, 254–265 (1985).

_Primary Examiner_—Robert J. Warden
_Assistant Examiner_—Carol A. Spiegel
_Attorney, Agent, or Firm_—Ian C. McLeod

[57] ABSTRACT

A method for determining lipids using thin layer chromatography and multiple enzymatic staining is described. The method uses a hydrolase enzyme, an oxidase enzyme and a peroxidase enzyme in the presence of a chromogen precursor to form an oxidized chromogen stain. The method is particularly useful in determining phospholipids from animal and human tissue and/or fluids.

15 Claims, 3 Drawing Sheets

CHOLESTEROL

CHOLESTEROL-ESTER + H$_2$O $\xrightarrow{\text{CEH}}$ CHOLESTEROL + FATTY ACID

CHOLESTEROL + O$_2$ $\xrightarrow{\text{CO}}$ ▲CHOLESTENONE + H$_2$O$_2$

2H$_2$O$_2$ + 4-AAP + HDCBS $\xrightarrow{\text{POD}}$ OXIDIZED DYE COMPLEX + H$_2$O

PHOSPHOLIPIDS (PHOSPHATIDYLGLYCEROL)
PHOSPHATIDYLCHOLINE + H$_2$O $\xrightarrow{\text{PL-D}}$ PHOSPHATIDIC ACID + CHOLINE + GLYCEROL
(SPHINGOMYELIN)            (PHOSPHOCERAMIDE)

CHOLINE + O$_2$ $\xrightarrow{\text{COD}}$ BETAINE ALDEHYDE + H$_2$O$_2$

BETAINE ALDEHYDE + H$_2$O      BETAINE + H$_2$O$_2$

GLYCEROL + ATP $\xrightarrow{\text{GK}}$ GLYCEROL 3-PHOSPHATE + ADP

GLYCEROL 3-PHOSPHATE + O$_2$ $\xrightarrow{\text{GPO}}$ DIHYDROXYACETONE PHOSHATE + H$_2$O$_2$ 2H$_2$O$_2$ + 4-AAP + DCN $\xrightarrow{\text{POD}}$ OXIDIZED DYE COMPLEX

TRIGLYCERIDES

TRIGLYCERIDES + 3H$_2$O $\xrightarrow{\text{LIPASE}}$ GLYCEROL + 3 FATTY ACIDS

GLYCEROL + ATP $\xrightarrow{\text{GK}}$ GLYCEROL-3-PO$_4$ + ADP

GLYCEROL-3-PO$_4$ + O$_2$ $\xrightarrow{\text{GPO}}$ DHAP + H$_2$O$_2$

2H$_2$O$_2$ + 4-AAP + HDCBS $\xrightarrow{\text{POD}}$ OXIDIZED DYE COMPLEX + H$_2$O

FIG. 2

METHOD FOR DETERMINING LIPIDS

BACKGROUND OF THE INVENTION

(1) Field of the Invention

The present invention relates to a method for determining lipids using thin layer chromatography (TLC) to separate the lipids and then multiple enzyme catalyzed steps culminating in chromogen staining of the TLC separated lipids. In particular, the present invention relates to a method which uses a hydrolase enzyme, an oxidase enzyme and a peroxidase enzyme in the presence of a chromogen precursor to form an oxidized chromogen stain.

(2) Prior Art

Lipids are fatty acid esters and particularly include triesters of glycerol. Phospholipids are lipids characterized by the formula:

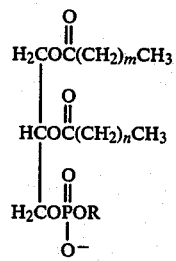

where m and n are an integer between 10 and 16 and R is selected from various groups. Lipids include cholesterol, lecithin, cephalin and the like. The compounds are characterized by diester linkages and a phosphate group. The determination of lipids, particularly phospholipids, in human and animal tissue and serum is important in relation to neoplastic disorders, diabetes mellitus, arteriosclerosis, coronary heart disease, extra hepatic obstruction detection and amniotic fluid analysis.

Conventional electrophoretic systems separate molecules by charge and molecular weight. However, when the molecular weight and charges of the molecules are similar, alternate fractionation procedures must be used. Thin layer chromatography (TLC) can separate the components in a mixture based on their polarity. Phospholipids, naturally occur as a heterogenous mixture of individual compounds of variable polarity whose molecular weights are similar and usually less than 1000 and are particularly difficult to identify. TLC has provided a tool to separate and quantitate phospholipids as well as other lipids.

Current methods of TLC phospholipid quantitation employ charring with sulfuric acid (Gluck, L., et al. Am. J. Obstet Gynecol Ref 120,142-155 (1974)), chemical determination of the phosphate groups (Kolins, M. D., et al, Clin. Chem. 26, 403-405 (1980)) and determination with anagolene sodium, i.e. Coomassie dye (Nakamura, K., and Handa, S., Anal. Biochem. 142, 406-410 (1984)). None of these staining procedures are specific for the phospholipids. Furthermore, phospholipid determination by sulfuric acid presents inherent quantification problems due to variable charring of the phospholipid classes (Gluck, L., et al, Clin. Perinatol 1, 125-131 (1974)). Recently, enzymic procedures for the determination of lecithin, sphingomyelin and phosphatidylglycerol in aqueous solution have been developed. McGowan, M. W., et al, J. Clin. Chem. Clin Biochem, 20 807-812 (1982); McGowan, M. W., et al, Clinical Chemistry 29 1513-1517 (1983); Artiss J. D., et al Clinical Chem 30 534-537 (1984); McGowan, M. W., et al, Microchemical Journal 31 216-223 (1985); Bozinowski, D. et al Microchemical Journal 32, 254-265 (1985); Artiss, J. D. Annals of Clin. and Lab Science 15 488-494 (1985). This procedure allows only a single determination in a given solution.

Other prior art includes Han J. et al, Korean J. Biochem 17(1) 19-30 (1985); Higashi, H, Seikagaku 57(2) 133-135 (1985) and Ambrosetti, P., Chromatographic 9(12) 633-634 (1976). The Ambrosetti reference describes bromine oxidized phosphate esters which inhibit enzyme activity. The stained areas are separate from the oxidized phosphate esters where enzyme activity is not inhibited. Bromine is difficult to handle in the laboratory. Higashi uses antibodies. Han describes TLC and an enzymatic assay with an enzyme attached to an antibody label. None of the procedures are regarded as being quantitative.

Objects

It is therefore an object of the present invention to provide a very sensitive quantitative method using TLC enzymatic staining for chromogen development. Further, it is an object of the present invention to provide a method which is simple and economical to perform. These and other objects will become increasingly apparent by reference to the following description and the drawings.

In the Drawings

FIG. 2 is a schematic of some of the enzymatic reactions used in the present invention.

GENERAL DESCRIPTION

The present invention relates to a method for the determination of mixed lipids in a liquid which comprises: providing a thin layer chromatographic plate having a thin stationary phase; providing the liquid to the stationary phase so that the mixed lipids separate into separated bands of individual lipids; reacting the individual lipids with an aqueous solution comprising a hydrolase enzyme, an oxidase enzyme, a peroxidase enzyme and chromogen precursor(s), wherein the hydrolase enzyme catalyzes ester hydrolysis products from the lipids, the oxidase enzyme produces hydrogen peroxide by reaction with the hydrolysis products which in turn reacts with the chromogen precursor to form an oxidized chromogen complex which is water insoluble in the presence of the peroxidase enzyme.

The present invention particularly relates to a method wherein enzymes are used to develop a reagent to determine phospholipids particularly lecithin (L), sphingomyelin (S) and phosphatidyloglycerol (PG) simultaneously on a TLC plate.

Figure 1:
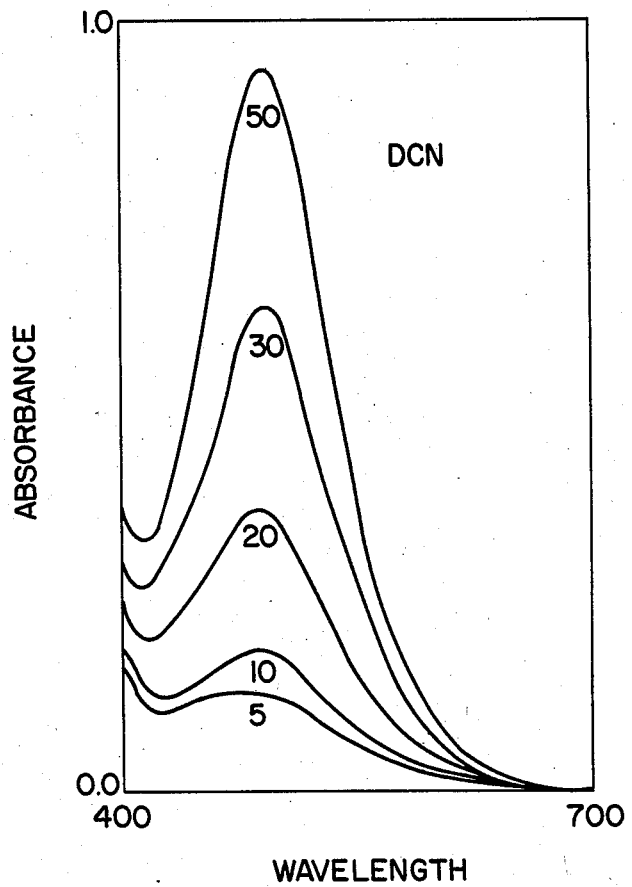
FIG. 1 is a graph showing the spectra for 2,4-dichloro-1-naphthol (DCN) a preferred insoluble chromogen precursor coupled to 4-aminoantipyrine.

An aqueous insoluble chromogen was needed as the electron donor in a peroxidase (POD) coupling reaction as shown in FIG. 2. In addition, the chromogen needed to generate a high absorptivity value that was similar to 2-hydroxy-3,5-dichlorobenzenesulfonate (HDCBS) used in the aqueous solution procedures of the prior art. Insoluble peroxidase substrates, commonly used in histochemistry, were investigated. The carcinogenic hazards associated with benzidine compounds deemed them less suitable for use in a routine laboratory procedure. Since 4-chloro-1-naphthol was found to be an acceptable substitute for benzidine as a myeloperoxidase substrate it was decided to investigate the analogs naphthol and 2,4-dichloro-1-naphthol as well. In order to evaluate the efficacy of the chromogens, the molar absorptivity was determined and compared to the soluble chromogens phenol and HDCBS. The molar absorptivities (liters per mole centimeter) of the compounds were; phenol=12,600 $Lmol^{-1}cm^{-1}$, naphthol=16,800 $Lmol^{-1}cm^{-1}$, 4-chloro-1-naphthol=25,6000 $Lmol^{-1}cm^{-1}$, 2,4-dichloro-1-naphthol=38,400 $Lmol^{-1}cm^{-1}$, HDCBS=52,000 $Lmol^{-1}cm^{-1}$. The molar absorptivities of naphthol, 4-chloro-1-naphthol and 2,4-dichloro-1-naphthol were determined at 495 nm while phenol and HDCBS were determined at 505 nm and 510 nm respectively. The disubstituted naphthol, 2 4-dichloro-1-naphthol (DCN) was chosen as the chromogen for the enzymic phospholipid determination on TLC plates because of its high absorptivity. The spectra of DCN and peroxidase with 5 to 50 micromoles of peroxide is shown in FIG. 1. The scans from 700 nm to 400 nm indicate the peak wavelength at 495 nm. Furthermore, except for the hypsochromic shift, the spectra of DCN is similar to HDCBS.

The reaction scheme for the simultaneous enzymic determination of phospholipids is shown in FIG. 2. Phospholipase D (PL-D) hydrolyzes phosphatidylglycerol to phosphatidic acid plus glycerol, phosphatidylcholine (lecithin) to phosphatidic acid plus choline and sphingomyelin to phosphoceramide plus choline. The choline is oxidized to betaine plus two hydrogen peroxides in a two step reaction catalyzed by choline oxidase (COD). The glycerol is phosphorylated in the presence of adenosine 5'-triphosphate (ATP) and glycerol kinase (GK). The glycerol-3-phosphate is oxidized to dihydroxyacetone phosphate plus hydrogen peroxide by glycerol phosphate oxidase (GPO). Finally, the hydrogen peroxide generated from each phospholipid is used by peroxidase (POD) to enzymatically couple 4-aminoantipyrine (4-AAP) and 2,4-dichloro-1-naphthol (DCN) to form an oxidized chromogen complex with a maximum absorbance at 495 nm. The procedure for the glycerides is similar and is shown in FIG. 2.

SPECIFIC DESCRIPTION

Materials and Procedure

Phospholipid Mobile Phase

The mobile phase consisted of chloroform/methanol/ammonium hydroxide (65:30:3 by vol.). Other solvent mixtures can be used depending upon the lipids to be separated.

Phospholipid Phosphate stain

The molybdate reagent (Kolins, M. D., et al, Clin. Chem. 26, 403–405 (1980)) was prepared by combining 50 mL of 2.52 mol/L sulfuric acid, 5 mL of 8.2 mmol/L antimony potassium tartrate, 15 mL of 32.3 mmol/L ammonium molybdate and 30 mL of 100 mmol/L ascorbic acid. The active stain was prepared by combining 8 mL of molybdate reagent with 1 mL of isopropanol and 13 mL of distilled water.

Phospholipid Enzymic stain

The reagent mixture was prepared to contain phospholipase D, 5kU/L; choline oxidase, 5kU/L; glycerol kinase, 2kU/L; glycerophosphate oxidase, 5kU/L; peroxidase, 17kU/L; adenosine 5'-triphosphate, 1 mmol/L; magnesium chloride, 10 mmol/L; calcium chloride, 15 mmol/L and 4-aminoantipyrine, 2 mmol/L in a 100 mmol/L tris-HCl buffer (pH 7.6). 2,4-dichloro-1-naphthol was dissolved in water containing 8% (w/v) Triton X-100 to contain 25 mmo/L.

Phospholipid Standards

The standards were prepared in chloroform to contain lecithin, 5 mmol/L; sphingomyelin, 5 mmol/L and phosphatidylglycerol, 5 mmol/L.

Procedures

Densitometry

Densitometric scans at various wavelengths were obtained using a slit width of 5 mm (long dimension of the zone) and a slit length (width of the zone) of 0.5 mm. Relative percentages of the peaks were obtained by built-in electronic integration. Densitometric linearity was assured by scanning a densitometer standard containing predetermined relative areas.

Thin Layer Chromatography

The silica TLC plates were heat activated in a 110° C. convection oven for 30 minutes. The plates were allowed to cool to room temperature prior to sample application.

Sample Application 10 microL aliquots of the phospholipids dissolved in chloroform were applied as streaks about 1 cm long or as spots about 1 cm long to the chromatography plate. The plates were placed in a reduced pressure desiccator for 5 minutes. 100 mL of the mobile phase was poured into the short-bed continuous-development chamber and the plates were positioned for minimum solvent velocity. Development was allowed to proceed for 40 minutes. The plates were removed from the chamber and air dried with a cool hair dryer.

Phospholipid Phosphomolybdate Stain

The active stain was prepared just prior to use and poured over the TLC plate. After 1 minute the plate was removed from the stain and dried with warm air until blue phospholipid bands developed. The bands were stable for only 8 to 12 hours and therefore a photographic record was made.

Phospholipid Enzymic Stain

Just prior to use, 1 ml of 2,4-dichloro-1-naphthol (DCN) solution was added to 19 mL of the enzyme reagent mixture with stirring. This reagent is stable for at least 8 hours when stored at 4° C. The reagent was then poured into a staining dish which contained the TLC plate. Incubation was allowed to proceed at 37° C. for 30 minutes or until orange-red bands, corresponding to the phospholipids, developed. Following this incubtion the plate was rinsed with water and dried at 47° C.

under reduced pressure. Although the bands were stable for at least 1 month a photographic record was made.

Figure 3:
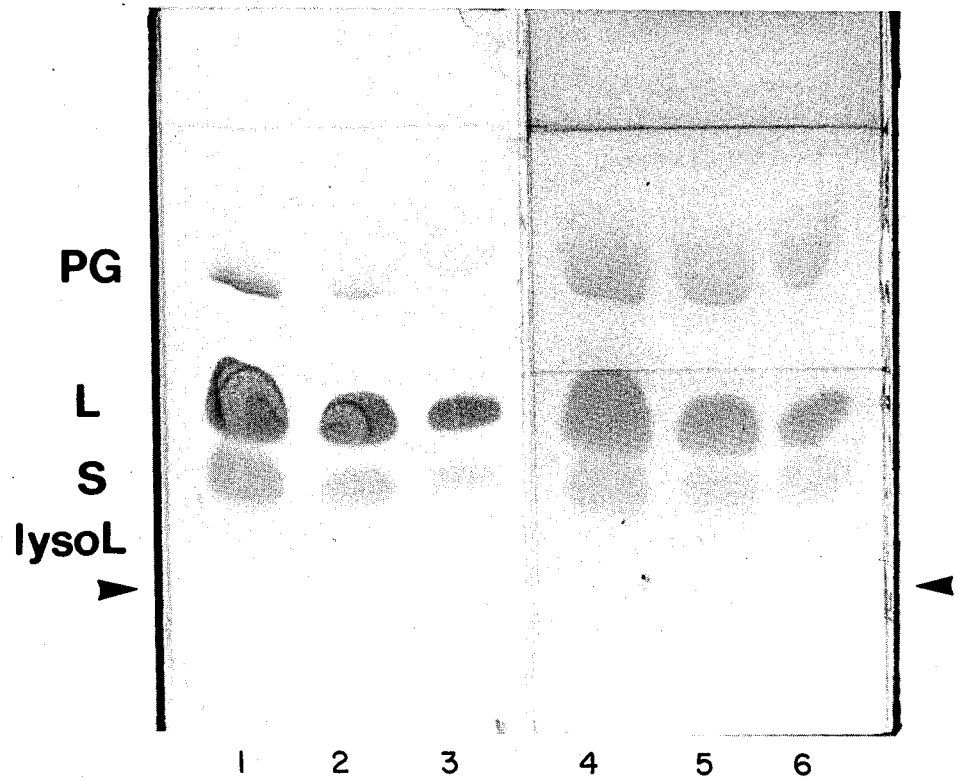
FIG. 3 is a photograph showing a chromatogram developed according to the method of the present invention and the prior art.

A photograph of the TLC plates stained with molybdenum (lanes 1,2,3) as in the prior art and the enzymic stain (lanes 4,5,6) is shown in FIG. 3. Lanes 1 and 4 have phosphatidylglycerol (PG) concentrations of 3 mmol/L, lecithin (L) concentrations of 10 mmol/L and sphingomyelin (S) concentrations of 5 mmol/L. Lanes 2 and 5 have 1.5 mmol/L of PG, 5 mmol/L of L and 2.5 mmol/L of S while lanes 3 and 5 have 0.75 mmol/L of PG, 2.5 mmol/L of L and 1.25 mmol/L of S. The position of each phospholipid on the chromatogram can be expressed as the ratio $R_f$=migration distance of the phospholipid from the origin: migration distance of the solvent front from the origin. It is apparent that the migration distances of the phospholipids and the solvent front in all lanes are essentially the same. An average of the migration distances of the 6 lanes indicates that the $R_f$ for $S=1.47/6.3=0.25$, for $L=2.47/6.3=0.39$, for $PG=4.34/6.3=0.69$ and for lysolecithin (lysoL)$=0.7/6.3=0.11$. The lysolecithin observed on the enzymic stained plate (lanes 4,5,6) was a contaminant of the lecithin standard. It is obvious that the molybdenum stain was not sensitive enough to detect the contaminant. Furthermore, the black and white photograph of the TLC plates discriminates against the rose-colored enzyme bands while the blue molybdate bands appear to be more intense when in fact the enzymic stained bands are more intense at peak wavelength. Those skilled in the art will know that the $R_f$ values may change by substitution of a different TLC plate into the procedure.

Figure 4:
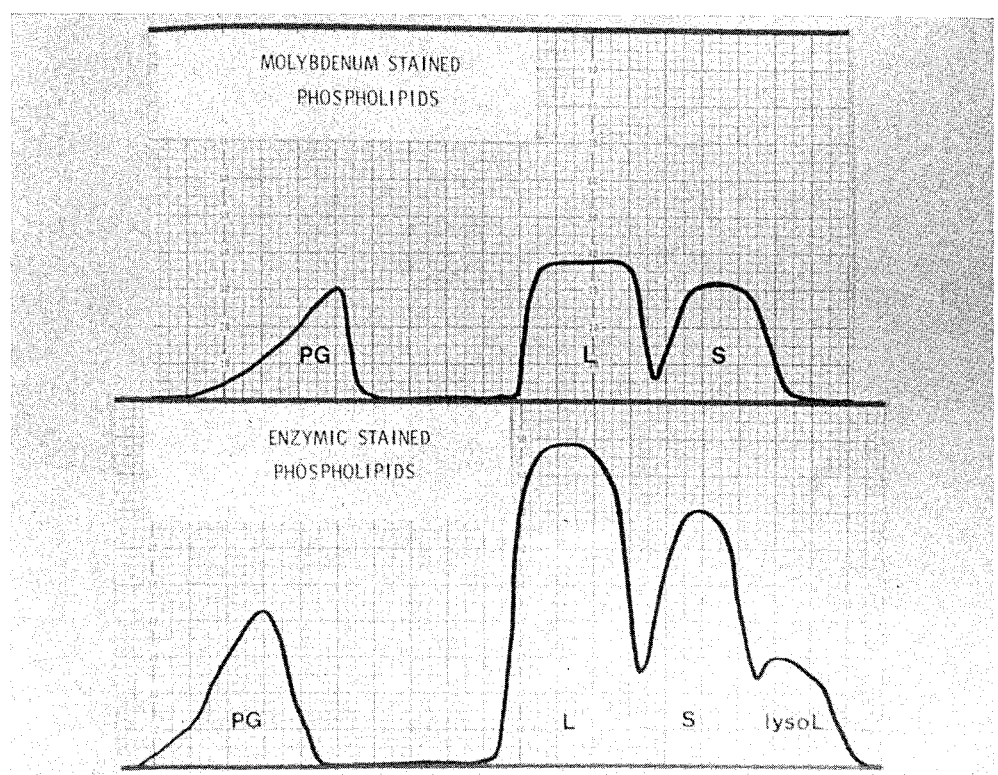
FIG. 4 is a densitometric scan of chromatographically separated phosphatidylglycerol (PG), lecithin (L), sphingomyelin (S) and Lysolecithin (lysol) visualized by phosphomolybdate of the prior art (Top) and TLC enzymatic staining (bottom) according to the present invention.

FIG. 4 demonstates the increased sensitivity of the enzymic stain relative to the molybdenum stain. Densitometry was performed on the intermediate concentration level of phospholipids as seen in lanes 2 and 5 at a wavelength of 620 nm for the molybdenum stained phospholipids and at 495 nm for the enzymic stained phospholipids. The contaminant, found to be lysolecithin, shows a distinct band when visualized with the enzyme stain. The data in Table 1 quantitiatively compares the concentrations of the phospholipids as determined by the current molybdenum stain and the dichloro-naphthol enzymic stain. The counts indicate that the enzymic stained phospholipids generate a 2 fold increase in absorbance over the molybdenum stain. The calculated lecithin and sphingomyelin values are similar for both procedures if the lysolecithin band is ignored. However, since the lysolecithin was a contaminant of the lecithin the observed concentration of lecithin is lower than expected. If the counts generated by lysolecithin were added to the lecithin counts (L=56%) the final L/S ratio for the enzymic plate would be 25% greater than for the molybdenum stained plate. Furthermore, based on the molar concentration of phospholipids added, the expected relative percents are 17% PG, 55% L and 28% S which more closely corresponds to the enzymic results. Thus the enzymic determination of TLC separated phospholipids is more accurate and sensitive than the conventional molybdate method although it is a more time consuming procedure due to the incubation required for the coupled enzymic reactions to reach completion. However, this is a minor disadvantage and does not deter its use as a clinical procedure.

The procedure of the foregoing example was repeated with other lipids, enzymes and chromogens. Numerous variations will occur to those skilled in the art.

We claim:

1. A method for the determination of mixed lipids in a liquid which comprises:
   (a) providing a thin layer chromatographic plate having a stationary phase as the thin layer which separates the mixed lipids;
   (b) applying the liquid containing the mixed lipids to the stationary phase on the plate so that the mixed lipids separate into separated bands of individual lipids upon migration with a mobile phase;
   (c) reacting the individual lipids with an aqueous solution comprising a hydrolase enzyme, an oxidase enzyme, a peroxidase enzyme and chromogen precursor(s), wherein the hydrolase enzyme catalyzes ester hydrolysis products from the lipids, the oxidase enzyme produces hydrogen peroxide by reaction with the hydrolysis products which in turn reacts in the presence of the peroxidase enzyme with the chromogen percursor(s) to form an oxidized chromogen complex(es) which is water insoluble so that the chromogen complex(es) remains in the band on the stationary phase; and
   (d) determining the individual lipids in the thin stationary phase by means of the chromogen complex(es).

2. The method of claim 1 wherein the mixed lipids comprise a cholesterol-fatty acid ester which is hydrolyzed to cholesterol and a fatty acid with the hydrolase enzyme and wherein the cholesterol is oxidized by the oxidase enzyme to produce the hydrogen peroxide.

3. The method of claim 2 wherein the oxidase enzyme is cholesterol oxidase.

4. The method of claim 2 wherein the hydrolase enzyme is cholesterol ester hydrolase.

5. The method of claim 1 wherein the mixed lipids are selected from a phosphatidylcholine and a phosphatidylglycerol which are hydrolyzed by the hydrolase enzyme to a phosphatidic acid and choline or glycerol and wherein the choline or glycerol are oxidized by an oxidase enzyme to produce the hydrogen peroxide.

6. The method of claim 5 wherein the hydrolase enzyme is phosphatidylcholine phosphatidohydrolase.

7. The method of claim 6 wherein the oxidase enzyme is choline:oxygen 1-oxidoreductase.

8. The method of claim 1 wherein the mixed lipids comprises a triglyceride which is hydrolyzed by the hydrolase enzyme to fatty acids and to glycerol and wherein the glycerol is phosphorylated with ATP in the presence of glycerol kinase and then oxidized with glycero-3-phosphate oxidase as the oxidase enzyme to produce hydrogen peroxide.

9. The method of claim 1 wherein the mixed lipids comprises phosphatidylglycerol which is hydrolyzed by phospholipase D to produce glycerol which is in turn phosphorylated by ATP in the presence of glycerol kinase and then oxidized with glycero-3-phosphate oxidase as the oxidase enzyme to produce hydrogen peroxide.

10. The method of claim 1 wherein the chromogen is coupled with peroxidase as the peroxidase enzyme.

11. The method of claim 10 wherein the chromogen precursor is mixed 4-aminoantipyrine and 2,4-dichloro-1-naphthol which react in the presence of hydrogen peroxide and the peroxidase enzyme to form the oxidized chromogen complex(es).

12. The method of claim 1 wherein the mixed lipids comprise a cholesterol fatty acid, a phosphatidyl choline and a triglyceride.

13. The method of claim 1 wherein the mixed lipids comprise sphingomyelin which is hydrolyzed to phosphoceramide and choline and wherein the choline is oxidized by the oxidase enzyme to produce the hydrogen peroxide.

14. The method of claim 13 wherein the oxidase enzyme is choline:1-oxidoreductase.

15. The method of claim 1 wherein the chromogen complex(es) is determined with a densitometer measuring light absorbance by the chromogen complex(es).

* * * * *

UNITED STATES PATENT AND TRADEMARK OFFICE
CERTIFICATE OF CORRECTION

PATENT NO. : 4,784,945
DATED : November 15, 1988
INVENTOR(S) : Joseph D. Artiss, Dennis Bozimowski, Robert J. McEnroe and Bennie Zak It is certified that error appears in the above—identified patent and that said Letters Patent is hereby corrected as shown below:

Column 3, line 21 "25,6000" should be --25,600--.

Column 4, line 14 "25 mmo/L." should be --25 mmol/L.--.

Column 6, line 63 before "peroxidase" (first occurrence) insert --horseradish--.

Signed and Sealed this

Second Day of May, 1989

Attest:

DONALD J. QUIGG

Attesting Officer

Commissioner of Patents and Trademarks